(12) United States Patent
Urushihara et al.

(10) Patent No.: US 6,632,958 B1
(45) Date of Patent: Oct. 14, 2003

(54) PROCESS FOR PRODUCING A PURIFIED PROSTAGLANDIN DERIVATIVE

(75) Inventors: Masahiro Urushihara; Yoshitomi Morizawa, both of Kanagawa (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/701,388

(22) PCT Filed: Jun. 3, 1999

(86) PCT No.: PCT/JP99/02975

§ 371 (c)(1),
(2), (4) Date: Dec. 4, 2000

(87) PCT Pub. No.: WO99/62877

PCT Pub. Date: Dec. 9, 1999

(30) Foreign Application Priority Data

Jun. 4, 1998 (JP) ............................. 10-156438

(51) Int. Cl.[7] ........................ C07C 69/74; C07C 69/34
(52) U.S. Cl. .................. 560/121; 560/121; 560/128; 560/190
(58) Field of Search ............... 560/121, 128, 560/190

(56) References Cited

U.S. PATENT DOCUMENTS 4,547,521 A * 10/1985 Guzzi et al.
5,120,870 A    6/1992 Mizushima et al.
5,194,670 A * 3/1993 Mizushima et al.

FOREIGN PATENT DOCUMENTS

JP          8-119934        5/1996
JP          11-158120       6/1999

* cited by examiner

Primary Examiner—Gary Geist
Assistant Examiner—Farhad Forohar
(74) Attorney, Agent, or Firm—Oblon, Spivak, McClelland, Maier & Neustadt, P.C.

(57) ABSTRACT

An alkene (1) is added to cyclopentenone (2) under the action of an alkyl lithium and an organic copper reagent to form an adduct, said adduct is reacted with e.g. a carboxylic anhydride (4) to obtain a prostaglandin derivative (6), which is then treated with a nitrogen-containing compound such as 2,2'-bipyridyl to efficiently remove the organic copper reagent used in the synthesis and by-products derived from said reagent, to obtain a purified prostaglandin derivative (6) having a high purity:

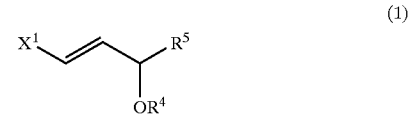

(1)

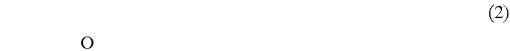

(2)

$R^1X^2$ (3)

$(R^1)_2O$ (4)

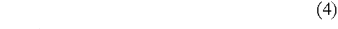

$R^1OR^6$ (5)

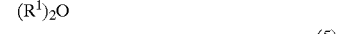

(6)

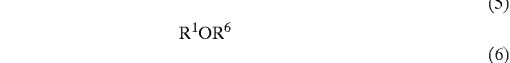

23 Claims, No Drawings

PROCESS FOR PRODUCING A PURIFIED PROSTAGLANDIN DERIVATIVE

TECHNICAL FIELD

The present invention relates to a process for producing a purified prostaglandin derivative.

BACKGROUND ART

Since six structures of prostaglandins (hereinafter prostaglandin will be referred to as PG) $PGE_1$, $PGE_2$, $PGE_3$, $PGF_{1\alpha}$, $PGF_{2\alpha}$ and $PGF_{3\alpha}$ had been determined in 1960, PG analogues have been found one after another, and their biological activities have also been clarified one after another. Specifically, their various biological activities become known such as a platelet aggregation inhibitory action, a diastolic blood pressure lowering action, a gastric-acid secretion inhibitory action, a smooth muscle contraction action, a cell protection action and a diuresis action. Further, it is also known that PGs are a class of compounds which are effective for treatment or prevention of e.g. myocardial infarction, angina pectoris, arterial sclerosis, hypertension, duodenal ulcer, induction of labor and artificial termination of pregnancy.

Meanwhile, according to literature, pharmaceuticals comprising such PGs are expected to have an important role in future. PGs are typical local hormones, which are produced locally as the case requires and act locally. Accordingly, it is proposed that a drug delivery system taking properties as an autacoid and chemical properties into consideration is necessary for such PGs-related pharmaceuticals. The drug delivery system is a system to improve the value of a pharmaceutical having such a drawback that it has a weak effect when administered systemically and will cause strong systemic side effects. As one example of the drug delivery system of the PGs, lipid microspheres (hereinafter referred to as LMs) as carriers, are mentioned. The LMs are considered as emulsified fine particles of PG-containing lipid practically, and referred to also as a fat emulsion. The fat emulsion-PG as mentioned hereinafter means an emulsified lipid containing a PG.

Conventionally, a target therapeutic agent comprising fat emulsion-$PGE_1$ having $PGE_1$ contained in LMs with a diameter of 2 μm has been reported to have high stability in the body and to show higher vasodilator action and platelet aggregation inhibitory action as compared with $PGE_1$ alone (Sim, A.K., et al., Arzneim-Forsch/Drug Res., 1206–1209, 1986).

However, if the fat emulsion-$PGE_1$ is administered to the body, a large amount of $PGE_1$ will be released from the LMs. Accordingly, a study has been made to suppress the release amount by employing fat emulsion-$PGE_1$ ester (Igarashi et al, Ensho (Inflamation), 8,243–246, 1988). Specifically, it was confirmed that a $PGE_1$ ester had no activity and that the $PGE_1$ ester was cut at the ester linkage by an esterase in the body to form $PGE_1$ and to exhibit activity (such a $PGE_1$ ester is called prodrug of $PGE_1$) firstly, and then the stability of the fat emulsion-$PGE_1$ ester in blood was studied.

In said study, as the $PGE_1$ ester, a methyl ester, an ethyl ester, a butyl ester or an octyl ester was used. As the index indicating the activity of the $PGE_1$ ester, a platelet aggregation inhibitory action was employed. Further, the stability as the fat emulsion in blood was evaluated by measuring the release of the $PGE_1$ ester from LMs when incubated in an isotonic salt solution. As a result, the storage stability and effectiveness of LM preparations of $PGE_1$ esters were confirmed.

Here, in production of the fat emulsion, it is necessary to finely disperse the fat emulsion-$PGE_1$ in a dispersion medium so as to increase sustained release of the fat emulsion-$PGE_1$. In such a case, the $PGE_1$ and the other materials are dissolved under heating, followed by homogenization in water at a high temperature of a level of from 80 to 90° C. However, a conventional $PGE_1$ quickly decompose under such a high temperature. Further, a conventional $PGE_1$ quickly decompose also in commercial distribution channel since it has a low storage stability. Accordingly, it has been proposed to develop $PGE_1$ analogues having a good stability even when prepared at a high temperature, and having an improved storage stability also in distribution channel. For example, a $PGE_1$ analogue having a carbonyl group at the 9-position modified with an enol ester has been reported (Japanese Pat. No. 2,602,964).

As a method of synthesizing such a PG derivative, a method of using an organic copper reagent is mentioned. Further, a method of adding e.g. an organic phosphorus compound or an organic sulfur compound to coordinate such a compound with the organic copper reagent, with a purpose of increasing the solubility of said organic copper reagent in a reaction solvent, may be mentioned. In a case where a PG derivative is synthesized by said method, compounds used for the reaction and by-products derived from said compounds are present in the PG derivative. If it is attempted to remove them by a conventional after-treatment such as extraction operation, it is difficult to completely remove them. Further, if it is attempted to remove such compounds by a purification method such as column chromatography, the number of steps will increase, such being inefficient, and the yield may decrease in the after-treatment process.

DISCLOSURE OF THE INVENTION

Namely, the present invention has been made to overcome the problems mentioned above, and provides a process for producing a purified prostaglandin derivative, which comprises adding an alkene represented by the following formula (1) to cyclopentenone represented by the following formula (2) under the action of an alkyllithium and an organic copper reagent to form an adduct, reacting said adduct with a carboxylic halide represented by the following formula (3), a carboxylic anhydride represented by the following formula (4) or a mixed carboxylic anhydride represented by the following formula (5) to obtain a reaction product containing a prostaglandin derivative represented by the following formula (6), and then treating said reaction product with a nitrogen-containing compound:

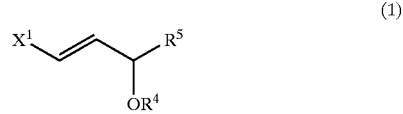

(1)

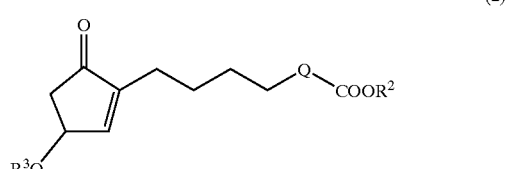

(2)

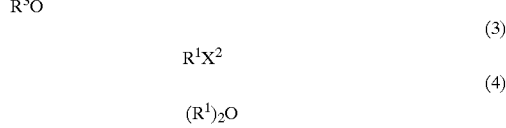

$R^1X^2$ (3)

$(R^1)_2O$ (4)

$R^1OR^6$ (5)

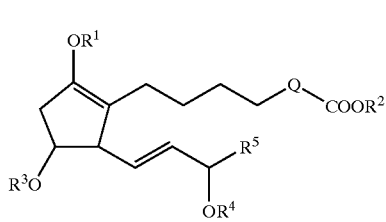

(6)

provided that symbols in the formulas represent the following meanings:

$R^1$ is an alkanoyl group or an alkanoyl group containing a hetero atom in the alkyl group moiety, $R^2$ is an alkyl group or an alkyl group containing a hetero atom, each of $R^3$ and $R^4$ which are independent of each other, is a protecting group for a hydroxyl group or a hydrogen atom, $R^5$ is an alkyl group, a substituted alkyl group, a cycloalkyl group, a substituted cycloalkyl group, an alkenyl group or an alkynyl group, $R^6$ is an alkanoyl group or an alkanoyl group containing a hetero atom in the alkyl group moiety, and is different from $R^1$.

Q is an ethylene group or a vinylene group, $X^1$ is an iodine atom or a trialkyltin group, and $X^2$ is a halogen atom.

$X^1$ in the alkene represented by the formula (1) (hereinafter referred to as alkene (1), the same applies to the other compounds) is an iodine atom or a trialkyltin group, and as the trialkyltin group, a tributyltin group is preferred. $X^1$ is preferably an iodine atom.

$R^4$ in the alkene (1) is a protecting group for a hydroxyl group or a hydrogen atom. As the protecting group for a hydroxyl group, protecting groups as described in literature by Greene et al (Protective Groups in Organic Synthesis, John Wiley & Sons, 1981) may be used. Among them, preferred as the protecting group for a hydroxyl group, are an acyl group (such as an alkanoyl group containing a lower alkyl group, preferably an acetyl group etc., or an acryl group containing an aromatic ring, preferably a benzoyl group, a p-methylbenzoyl group or a p-phenylbenzoyl group etc.), a trialkylsilyl group (such as a trimethylsilyl group or a t-butyldimethylsilyl group), a triarylsilyl group, an alkyldiarylsilyl group, an aryldialkylsilyl group, an aralkyl group (such as a benzyl group), a tetrahydropyranyl group and the like.

$R^5$ in the alkene (1) is an alkyl group, a substituted alkyl group, a cycloalkyl group, a substituted cycloalkyl group, an alkenyl group or an alkynyl group.

In a case where $R^5$ is an alkyl group, preferred is a linear or branched alkyl group having a carbon number from 3 to 8. Specific examples of said alkyl group include a butyl group, a pentyl group, a hexyl group, a 2-methylhexyl group, a heptyl group and an octyl group.

In a case where $R^5$ is a substituted alkyl group, preferred is a group having at least one hydrogen atom in a linear or branched unsubstituted alkyl group having a carbon number of from 3 to 8 substituted with a monovalent substituent, or a group having a bivalent hetero atom (such as an ethereal oxygen atom or a thioethereal sulfur atom) inserted between a carbon-carbon linkage of an alkyl group. As the monovalent substituent in the substituted alkyl group, preferred are a halogen atom, a haloalkyl group, an aryl group, an haloaryl group, an aryloxy group and a haloaryloxy group.

$R^5$ as the substituted alkyl group is preferably a haloalkyl group (such as a monohaloalkyl group or a dihaloalkyl group), an arylalkyl group, a (haloaryl)alkyl group, a phenoxyalkyl group or a (halophenoxy)alkyl group, particularly preferably a 1-fluoropentyl group, a 1,1-difluoropentyl group, a 1-fluoro-2-methylhexyl group, a phenoxymethyl group, a 2-chlorophenoxymethyl group, a 3-chlorophenoxymethyl group, a 4-chlorophenoxymethyl group, a 1-phenylethyl group or a 2-phenylethyl group, particularly preferably a phenoxymethyl group, a chlorophenoxymethyl group or a phenylethyl group.

In a case where $R^5$ is a cycloalkyl group, preferred is a cycloalkyl group having a ring moiety with a carbon number of from 3 to 8. The cycloalkyl group may be a cycloalkyl group having an alkyl group bonded to the ring moiety, and said alkyl group may be a linear or branched alkyl group having a carbon number of from 1 to 8. Specific examples of the cycloalkyl group include a cyclopropyl group, a cyclobutyl group, a cyclopentyl group, a 3-methylcyclopentyl group, a 3-ethylcyclopentyl group, a cyclohexyl group, a 4-methylcyclohexyl group, a cycloheptyl group and a cyclooctyl group.

In a case where $R^5$ is a substituted cycloalkyl group, preferred is a group having at least one hydrogen atom in the above-mentioned cycloalkyl group substituted. As the substituent, preferred is a halogen atom. The ring moiety in the substituted cycloalkyl group has a carbon number of preferably from 3 to 8. Specific examples of said substituted cycloalkyl group include a 2-fluorocyclopropyl group, a 3-fluorocyclobutyl group, a 3-chlorocyclobutyl group, a 3-fluorocyclopentyl group, a 3-chlorocyclopentyl group, a (chloro or fluoro)cyclohexyl group, a (chloro or fluoro)cycloheptyl group and a (chloro or fluoro)cyclooctyl group.

In a case where $R^5$ is an alkenyl group, preferred is a linear or branched alkenyl group having a carbon number of from 3 to 8. Specific examples of said alkenyl group include a 2-butenyl group, a 2-pentenyl group, a 2-hexenyl group, a 1-methyl-2-hexenyl group, a 2-heptenyl group, a 2-octenyl group and a 2-methyl-4-heptenyl group.

In a case where $R^5$ is an alkynyl group, preferred is a linear or branched alkynyl group having a carbon number of from 3 to 8. Specific examples of said alkynyl group include a 2-butynyl group, a 2-pentynyl group, a 2-hexynyl group, a 1-methyl-3-pentynyl group, a 1-methyl-3-hexynyl group and a 1-methyl-3-heptynyl group.

In a case where an asymmetric carbon is present in $R^5$, the stereochemistry of said carbon atom may be R, S or a mixture thereof.

Specific examples of the alkene (1) wherein $X^1$ is an iodine atom include the following compounds.

(1E,3S)-1-iodo-3-(t-butyldimethylsiloxy)-1-octene,
(1E,3R)-1-iodo-3-(t-butyldimethylsiloxy)-1-octene,
(1E,3S)-1-iodo-3-(t-butyldimethylsiloxy)-4,4-difluoro-1-octene,
(1E,3R)-1-iodo-3-(t-butyldimethylsiloxy)-4,4-difluoro-1-octene,
(1E,3S,5R)-1-iodo-3-(t-butyldimethylsiloxy)-5,9-dimethyl-deca-1,8-diene,
(1E,3S,5R or 5S)-1-iodo-3-(t-butyldimethylsiloxy)-5-methyl-1-none,
(1E,3S,4R or 4S)-1-iodo-3-(t-butyldimethylsiloxy)-4-methyl-1-octene-6-yne, and
(1E,3S,4R or 4S)-1-iodo-3-(t-butyldimethylsiloxy)-4-methyl-1-none-6-yne.

Specific examples of the alkene (1) wherein $X^1$ is a trialkyltin group include the following compounds.

(1E,3S)-1-tributylstannyl-3-(t-butyldimethylsiloxy)-1-octene, (1E,3R)-1-tributylstannyl-3-(t-butyldimethylsiloxy)-1-octene, (1E,3S)-1-tributylstannyl-3-(t-butyldimethylsiloxy)-4,4-difluoro-1-octene, (1E,3R)-1-tributylstannyl-3-(t-butyldimethylsiloxy)-4,4-difluoro-1-octene, (1E,3S,5R or 5S)-1-tributylstannyl-3-(t-butyldimethylsiloxy)-5,9-dimethyl-deca-1,8-diene, (1E,3S,5R or 5S)-1-tributylstannyl-3-(t-butyldimethylsiloxy)-5-methyl-1-none, (1E,3S,4R or 4S)-1-tributylstannyl-3-(t-butyldimethylsiloxy)-4-methyl-1-octene-6-yne, and (1E,3S,4R or 4S)-1-tributylstannyl-3-(t-butyldimethylsiloxy)-4-methyl-1-none-6-yne.

As the alkyl lithium, preferred is t-butyl lithium. The amount of the alkyllithium is preferably from 0.5 to 10 times, particularly preferably from 1 to 2 times, the molar quantity of the alkene (1).

As the organic copper reagent, preferred is a trialkylphosphine-copper iodide (I) complex, particularly preferred is a tri(n-butyl)phosphine-copper iodide (I) complex. The amount of the organic copper reagent is preferably from 0.2 to 4 equivalent amount, particularly preferably from 0.5 to 2 equivalent amount, based on the alkene (1). An organophosphorus compound or an organic sulfur compound may be added to the reaction system with a purpose of improving the solubility of the organic copper reagent. As the organic phosphorus compound, a trialkylphosphine is preferred, and tri(n-butyl)phosphine is preferred. As the organic sulfur compound, preferred are dimethylsulfide, diethylsulfide and diphenylsulfide. The amount of the organic phosphorus compound or the organic sulfur compound is preferably from 0.8 to 1.2 equivalent amount based on the organic copper reagent.

In the present invention, the alkene (1) is added to cyclopentenone (2) under the action of the alkyl lithium and the organic copper reagent.

In a case where $R^2$ in the formula (2) is an alkyl group, preferred is an alkyl group having a carbon number of from 1 to 8, particularly preferred is an alkyl group having a carbon number of from 1 to 5. Said alkyl group may be linear or branched. As $R^2$, particularly preferred is a methyl group, an ethyl group, a n-propyl group, an isopropyl group, a n-butyl group, an isobutyl group, a t-butyl group, a n-pentyl group, a n-hexyl group or a n-heptyl group, especially preferred is a methyl group, an ethyl group, a n-propyl group, an isopropyl group, a n-butyl group or a n-pentyl group.

In a case where $R^2$ is an alkyl group containing a hetero atom, preferred is a group having one or more hydrogen atom of an alkyl group substituted with a monovalent group containing a hetero atom. As the monovalent group containing a hetero atom, preferred is a monovalent group consisting of a hydroxyl group, an alkoxy group, a carboxyl group, an amino group or a carbamoyl group, or a monovalent group containing such a group. Further, the alkyl group moiety in the alkyl group containing a hetero atom may be linear or branched.

$R^2$ as the alkyl group containing a hetero atom, is preferably a 2-methoxyethyl group, a 3-methoxypropyl group, a 2-hydroxyethyl group, a 3-hydroxypropyl group, a carboxymethyl group, a 2-carboxyethyl group, a methoxycarbonylmethyl group, an ethoxycarbonylmethyl group, a carbamoylmethyl group, a (dimethylcarbamoyl)methyl group, a 2-(dimethylcarbamoyl)ethyl group, a 2-(dimethylamino)ethyl group or a 3-(dimethylamino)propyl group.

As $R^2$, preferred is an alkyl group containing a hetero atom, more preferred is said group having a carbon number of from 1 to 8 in the alkyl group moiety, particularly preferred is a said group having a carbon number of from 1 to 5 in the alkyl group moiety.

$R^3$ in the formula (2) is a protecting group for a hydroxyl group or a hydrogen atom, and as the protecting group for a hydroxyl group, preferred is a group similar to $R^4$. $R^3$ and $R^4$ may be the same or different.

Q in the formula (2) is an ethylene group ($-CH_2CH_2-$) or a vinylene group ($-CH=CH-$) In a case where Q is a vinylene group, said double bond may be a trans-double bond or a cis-double bond, and a trans-double bond is preferred.

In cyclopentenone (2), an asymmetric carbon atom is present at the 11-position by the carbon atom number of PG having prostanoic acid as a basic skeleton. However, the absolute configuration is not particularly limited.

In the present invention, the alkene (1) and cyclopentenone (2) are reacted under the action of the alkyllithium and the organic copper reagent to form an adduct. The amount of the alkene (1) is preferably from 0.5 to 10 times the molar quantity of cyclopentenone (2).

Said addition reaction is considered to proceed in the following mechanism. Namely, the alkene (1) reacts with an alkyllithium and undergoes lithiation to form a 1-lithioalkene having -$X^1$ in the alkene (1) substituted with -Li. Then, said 1-lithioalkene reacts with an organic copper reagent so that the 1-lithioalkene is formed into a complex at the terminal-Li with a copper atom to form organo copper. Then, said organo copper undergoes 1,4-conjugate addition with the cyclopentenone (2) to form an adduct.

Said reaction is carried out preferably in the presence of an inert solvent. As the inert solvent, preferred is an aprotic solvent, preferred are hexane, heptane, cyclohexane, dimethyl ether, diethyl ether, dioctyl ether, t-butylmethyl ether, tetrahydrofuran and 1,4-dioxane, etc., and particularly preferred is tetrahydrofuran or diethyl ether. In the case where an inert solvent is used, the amount is preferably from 1 to 500 times, particularly preferably from 10 to 100 times, the weight of the alkene (1).

The reaction temperature in said addition reaction is preferably from –95° C. to +50° C., particularly preferably from –78° C. to +20° C. Further, the reaction time is preferably from 0.1 to 20 hours. The adduct obtained by said addition reaction may be isolated as the case requires, but in the present invention, the adduct is preferably used directly for the subsequent reaction (hereinafter sometimes referred to as second step) without being taken out.

In the second step, the adduct is made to react with a carboxylic acid halide (3), a carboxylic anhydride (4) or a mixed carboxylic anhydride (5) to obtain a PG derivative (6). The amount of the carboxylic acid halide (3), the carboxylic anhydride (4) or the mixed carboxylic anhydride (5) is preferably from 0.5 to 50 times the molar quantity of the cyclopentenone (2). For this method, conditions in a known method for a known compound having a similar skeleton (Sih, et al., J. Am. Chem. Soc., 110, 3588, 1988) may entirely be applied.

$R^1$ in the carboxylic halide (3), the carboxylic anhydride (4) or the mixed carboxylic anhydride (5) is an alkanoyl group or an alkanoyl group containing a hetero atom in the alkyl group moiety.

In a case where $R^1$ is an alkanoyl group, preferred is an alkanoyl group having a carbon number of from 2 to 6, particularly preferred is an alkanoyl group having a carbon number of from 2 to 4, especially preferred is an acetyl group, a propionyl group, a isopropionyl group or a butanoyl group.

Further, in a case where $R^1$ is an alkanoyl group containing a hetero atom in the alkyl group moiety (hereinafter referred to as a substituted alkanoyl group), preferred is a substituted alkanoyl group having at least one hydrogen atom in the alkyl group moiety substituted with a monovalent group containing a hetero atom. As said monovalent group containing a hetero atom, preferred is a hydroxyl group, an alkoxy group, a carboxyl group, an amino group or a carbamoyl group, or a monovalent group containing such a group.

In the case where $R^1$ is an alkanoyl group, preferred mode is as follows. Namely, as the carboxylic anhydride (4), preferred is acetic anhydride or butyric anhydride. $R^6$ in the mixed carboxylic anhydride (5) is an alkanoyl group or an alkanoyl group containing a hetero atom in the alkyl group moiety, which is different from $R^1$, and preferred is an alkanoyl group similar to groups as mentioned as specific examples of $R^1$. As the mixed carboxylic anhydride (5), preferred is acetic acid-pivalic acid mixed anhydride (a compound wherein $R^1$ is an acetyl group and $R^6$ is a pivaloyl group) or butyric acid-pivalic acid mixed anhydride (a compound wherein $R^1$ is a butyryl group and $R^6$ is a pivaloyl group). As $X^2$ in the carboxylic acid halide (3), preferred is a chlorine atom, and as the carboxylic acid halide, preferred is acetyl chloride or butyryl chloride.

Further, in a case where $R^1$ is an alkanoyl group containing a hetero atom, preferred is the carboxylic acid halide (3) or the carboxylic anhydride (4), particularly preferred is 2-methoxypropionic anhydride, 2-methoxypropionyl chloride, 3-methoxypropionic anhydride, 3-methoxypropionyl chloride, 2-trimethylsiloxypropionic anhydride, 2-trimethylsiloxypropionyl chloride, 3-trimethylsiloxybutyric anhydride, 3-trimethylsiloxybutyryl chloride, trimethylsiloxycarbonylacetic anhydride, trimethylsiloxycarbonylacetyl chloride, methoxycarbonylacetic anhydride, methoxycarbonylacetyl chloride, ethoxycarbonylacetic anhydride, ethoxycarbonylacetyl chloride, dimethylaminoacetic anhydride, 4-(dimethylamino)butyryl chloride, 3-(dimethylamino)propionic anhydride or 3-(dimethylamino)propionyl chloride.

In the reaction of the second step, it is preferred to use a reaction solvent. As the reaction solvent, preferred is an aprotic solvent. As the reaction solvent, preferred are hexane, heptane, cyclohexane, dimethyl ether, diethyl ether, dioctyl ether, t-butylmethyl ether, tetrahydrofuran and 1,4-dioxane etc., and particularly preferred are tetrahydrofuran and diethyl ether. In the present invention, the adduct is made to react with the carboxylic acid halide (3), the carboxylic anhydride (4) or the mixed carboxylic anhydride (5) after the addition reaction preferably without being taken out. Accordingly, in the case of using a reaction solvent, it is preferred to use the same solvent as the reaction solvent in the addition reaction. One or more of the reaction solvents may be used.

The amount of the reaction solvent is preferably from 1 to 500 times the weight of the alkene (1). Further, the reaction temperature for the above-mentioned reaction is within a range of from −78° C. to a level of the temperature for the solvent reflux, preferably from −78° C. to a temperature in the vicinity of room temperature. The reaction time is preferably from 0.5 to 48 hours.

In the reaction mentioned above, a reaction product containing a PG derivative (6) will be formed.

$R^1$, $R^2$, $R^5$ and Q in the formula (6) are as defined above, and their preferred modes are also as defined above. Each of $R^3$ and $R^4$ is a protecting group for a hydroxyl group or a hydrogen atom. The PG derivative (6) useful as a pharmaceutical is a compound wherein both $R^3$ and $R^4$ are hydrogen atoms. However, in a case where $R^3$ and/or $R^4$ is a protecting group for a hydroxyl group, it is preferred to treat the PG derivative (6) with a nitrogen-containing compound without carrying out removal of the protecting group.

The PG derivative (6) wherein $R^3$ and/or $R^4$ is a protecting group for a hydroxyl group is represented by the formula (6a):

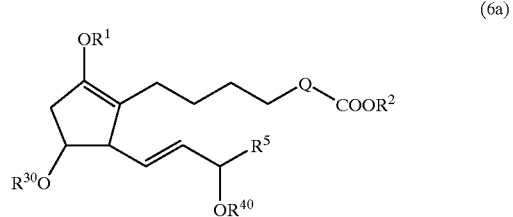

(6a)

provided that symbols in the formula represent the following meanings:

each of $R^1$, $R^2$, $R^5$ and Q is as defined above, each of $R^{30}$ and $R^{40}$ is a protecting group for a hydroxyl group or a hydrogen atom, and either one is a protecting group for a hydroxyl group.

Specific examples of a protecting group for a hydroxyl group as $R^{30}$ or $R^{40}$ include groups similar to the protecting groups for a hydroxyl group as $R^3$. Further, the PG derivative (6) or the compound represented by the formula (6a) has asymmetric carbon atoms at the 11-, 12- and 15-positions, whereby various stereoisomers are present. However, in the present invention, any PG derivative or a mixture thereof may be acceptable.

In the present invention, a reaction product containing the PG derivative (6) obtained by the above-mentioned reaction is treated with a nitrogen-containing compound.

As the nitrogen-containing compound, preferred is an organic carboxylic acid amide compound, an organic thiourea compound, an organic phosphorous triamide compound, an organic phosphoric triamide compound, an organic amine compound or an aromatic heterocyclic compound having a nitrogen atom as a hetero atom.

As the organic carboxylic acid amide compound, preferred is N,N-dimethylformamide, N,N-dimethylacetamide, urea, 1,3-dimethylurea, 1,1,3,3-tetramethylurea or 1,3-dimethyl-2-imidazolidinone etc.

As the organic thiourea compound, preferred is thiourea, 1,3-dimethyl-2-thiourea or 1,1,3,3-tetramethyl-2-thiourea etc.

As the organic phosphorous triamide compound, preferred is hexamethylphosphorous triamide or hexaethylphosphorous triamide etc.

As the organic phosphoric triamide compound, preferred is hexamethylphosphoric triamide or hexaethylphosphoric triamide etc.

The organic amine compound is an organic amine compound having a primary, secondary or tertiary amino group, and as the group to which said amino group is bonded, preferred is a linear aliphatic group, a branched aliphatic group, an alicyclic hydrocarbon group or an aromatic hydrocarbon group. As the organic amine compound, preferred are, for example, trimethylamine, triethylamine, triisopropylamine, tributylamine, trioctylamine, cyclohexylamine, pyrrolidine, piperidine, and N-methylcyclohexylamine, aniline, N-methylaniline and N,N-dimethylaniline.

Further, as the aromatic heterocyclic compound having a nitrogen atom as a hetero atom, preferred is a pyridine compound or a pyrimidine compound, and particularly preferred is the compound represented by the following formula (7):

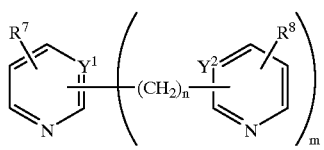

(7)

provided that symbols in the formula represent the following meanings:

each of $R^7$ and $R^8$ which are independent of each other, is a hydrogen atom or an alkyl group, each of $Y^1$ and $Y^2$ which are independent of each other, is a nitrogen atom or CH, provided that $Y^1$ to which $R^7$ is bonded is C, and $Y^2$ to which $R^8$ is bonded is C, n is an integer of from 0 to 5, and m is an integer of from 0 to 3.

In a case where $R^7$ is an alkyl group, preferred is an alkyl group having a carbon number of from 1 to 5, particularly preferred is a methyl group, an ethyl group or a propyl group etc.

As the compound represented by the formula (7), pyridine, 2-methylpyridine, 3-methylpyridine, 4-methylpyridine, 2-ethylpyridine, bipyridyl (such as 2,2'-bipyridyl), bis(2-pyridyl)methane, 1,2-bis(2-pyridyl)ethane, 1,3-bis(2-pyridyl)propane, 6,6'-bis(2-methylpyridyl) and 2,2'-bis(4-methylpyridyl) may, for example, be mentioned.

As the nitrogen-containing compound, preferred is an aromatic heterocyclic compound having a nitrogen atom as a hetero atom, and particularly preferred is a compound represented by the formula (7).

The nitrogen-containing compound is used to treat a crude reaction product immediately after the reaction with the carboxylic acid halide (3), the carboxylic anhydride (4) or the mixed carboxylic anhydride (5), or one obtained by subjecting said crude reaction product to a conventional purification method (such as filtration or column chromatography) (hereinafter they will generically be referred to as reaction product).

As a specific method of treatment with the nitrogen-containing compound, a method of mixing the reaction product with the nitrogen-containing compound, followed by stirring, may be mentioned. By said method, impurities in the reaction product, particularly the organic copper reagent used for the reaction or by-product derived from the organic copper reagent, will be removed. Said removal is considered to be attributable to the fact that the nitrogen-containing compound and the organic copper reagent or the by-product form a chelate. It has already been known that a nitrogen-containing compound and an organic copper compound form a chelate from literature (D. Purdie and A. F. Wells, J. Chem. Soc., 1503, 1936.), but the present invention is characterized by applying this to a purification method. By said purification method, unnecessary impurities alone can be removed efficiently without impairing formation of a desired compound.

The amount of the nitrogen-containing compound is preferably from 1 to 100 times the molar quantity of the organic copper reagent used for the reaction. Further, the temperature during the treatment with the nitrogen-containing compound is preferably from −20° C. to a temperature in the vicinity of room temperature, and the stirring time is preferably from 0.1 to 24 hours in the case of stirring.

It is preferred that the reaction solvent etc. is distilled off from the reaction product after treated with the nitrogen-containing compound, and then the reaction product is purified by a conventional purification method (such as silica gel column chromatography). A conventional purification method can adequately decrease the organic copper reagent or by-product derived from the organic copper reagent in the desired compound.

By the method mentioned above, a purified PG derivative (6) will be obtained. The copper content can be reduced to a level of from about 0 to about 100 ppm based on the purified PG derivative (6) by the method of the present invention. Further, in a case where the purified PG derivative is the PG derivative (6a) wherein $R^3$ and/or $R^4$ is a protecting group for a hydroxyl group, removal of the protecting group may be carried out as the case requires after the treatment with the nitrogen-containing compound. The removal of the protecting group may be carried out by a known method such as a method as described in literature by Greene et al (Protective Groups in Organic Synthesis, John Wiley & Sons, 1981) to obtain a purified product (6b) having the protecting group removed:

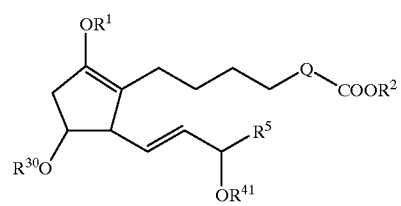

(6b)

provided that symbols in the formula represent the following meanings:

each of $R^1$, $R^2$, $R^5$ and Q is as defined for the formula (6a), and $R^{31}$ and $R^{41}$ are groups corresponding to $R^{30}$ and $R^{40}$, respectively, and they which are independent of each other, are a protecting group for a hydroxyl group or a hydrogen atom, provided that at least one of $R^{31}$ and $R^{41}$ corresponding to $R^{30}$ and $R^{40}$ as a protecting group for a hydroxyl group, is a hydrogen atom, and $R^{31}$ or $R^{41}$ corresponding to $R^3$ or $R^4$ as a hydrogen atom is a hydrogen atom.

The purified PG derivative (6) obtained by the method of the present invention is a compound with a high purity having the organic copper reagent used for the reaction or impurities derived from said reagent removed efficiently.

As said PG derivative (6), the following compounds may be mentioned.

Butyl 9-butanoyloxy-11α,15S-dihydroxyprosta-8,13E-dien-1-oate (the compound of the formula (6) wherein $R^1$ and $R^2$ are butyl groups, $R^3$ and $R^4$ are hydrogen atoms, Q is an ethylene group, and $R^5$ is a n-pentyl group), Butyl 9-butanoyloxy-11α,15S-bis(t-butyldimethylsiloxy) prosta-8,13E-dien-1-oate, Methyl 9-acetoxy-11α,15S-bis (t-butyldimethylsiloxy)-17S,20-dimethylprosta-8,13E-dien-1-oate, Methyl 9-acetoxy-11α,15S-dihydroxy-17S,20-dimethylprosta-8,13E-dien-1-oate, Methyl 9-acetoxy-11α,15S-bis(t-butyldimethylsiloxy)prosta-8,13E-dien-1-oate, Methyl 9-acetoxy-11α,15S-dihydroxyprosta-8,13E-dien-1-oate, Butyl 9-acetoxy-11α,15S-dihydroxy-17S,20-dimethylprosta-8,13E-dien-1-oate, Butyl 9-acetoxy-11α,15S-bis(t-butyldimethylsiloxy)-17S,20-dimethylprosta-8,13E-dien-1-oate, and Butyl 9-acetoxy-11α,15S-bis(t-butyldimethylsiloxy)-prosta-8,13E-dien-1-oate.

The purified PG derivative obtained by the present invention may be used as it is or as a pharmaceutical composition containing it. Said PG derivative is useful for treatment or prevention of myocardial infarction, angina pectoris, arterial sclerosis, hypertension, duodenal ulcer, induction of labor, artificial termination of pregnancy etc., and the purified PG derivative is useful as a preventive or therapeutic medicine for these.

BEST MODE FOR CARRYING OUT THE INVENTION

Next, the present invention will be explained in detail with reference to Examples. However, it should be understood that the present invention is by no means restricted thereto. The copper content was measured by inductively coupled plasma emission spectroscopy.

EXAMPLE 1

Example of Preparation of Purified Butyl 9-butanoyloxy-11α,15S-dihydroxyprosta-8,13E-dien-1-oate An ether (2.54 ml) solution of (1E,3S)-1-iodo-3-(t-butyldimethylsiloxy)-1-nonene (1.12 g, 3.03 mmol) was cooled to −78° C., and t-butyl lithium (3.84 ml of 1.48M pentane solution, 5.69 mmol) was dropwise added thereto in a stream of nitrogen. Stirring was carried out at the same temperature for 2 hours, and an ether (2.02 ml) solution of tri(n-butyl)phosphine-copper(I)iodide complex (1.04 g, 2.81 mmol) and tri(n-butyl)phosphine (0.69 ml, 2.76 mmol) was dropwise added thereto. The resulting mixture was stirred at −78° C. for 50 minutes, and an ether (8.07 ml) solution of (4R)-t-butyldimethylsiloxy-2-(6-butoxycarbonylhexyl)-2-cyclopenten-1-one (1.0 g, 2.53 mmol) was dropwise added thereto. The resulting mixture was stirred for 30 minutes at −78° C. and further for 30 minutes at from +30° C. to −20° C., to obtain an adduct.

To said adduct, butyric anhydride (1.12 ml, 6.83 mmol) was dropwise added at 0° C., and the resulting mixture was stirred at from 0° C. to room temperature for 2 hours. The mixture was poured into a saturated aqueous ammonium sulfate solution (43 ml) to separate an organic layer from an aqueous layer, the aqueous layer was extracted with ether (21 ml), and the resulting extract together with the above organic layer was dried over anhydrous magnesium sulfate to obtain a reaction product (copper content in said reaction product: 1–3%). The reaction product was subjected to filtration, and 2,2'-bipyridyl (2.06 g, 13.2 mmol) was added thereto, followed by stirring for 5 minutes. The solvent was distilled off under reduced pressure, and the obtained residue was purified by silica gel column chromatography (hexane: ethyl acetate=50:1–20:1 (volume ratio)) to obtain butyl 9-bkutanoyloxy-11α,15S-bis (t-butyldimethylsiloxy)prosta-8,13E-dien-1-oate (0.84.g, yield: 46.9%, copper content: 59 ppm) which was a PG derivative having a protecting group.

$^1$H-NMR(CDCl$_3$): δ 0.0–0.1(12H,m), 0.8–1.0(27H,m), 1.1–1.8(22H,m), 2.0(2H,m), 2.25(2H,t,J=7.5Hz), 2.39(3H,m), 2.8(1H,m), 3.05(1H,m), 4.05–4.15(4H,m), 5.3–5.6(2H,m).

Then, the PG derivative having a protecting group (700 mg, 0.99 mmol) was dissolved in acetonitrile (8.32 ml), and a 46% aqueous hydrofluoric acid solution (2.62 ml) was added thereto at 0° C., followed by stirring at the same temperature for 1 hour. The reaction liquid was poured into a liquid mixture of a 20% aqueous potassium carbonate solution (29 ml) and methylene chloride (5.9 ml), to separate an organic layer from an aqueous layer, the aqueous layer was extracted with methylene chloride (7.75 ml), the obtained extract together with the above organic layer was dried over anhydrous magnesium sulfate and subjected to filtration, and the solvent was distilled off under reduced pressure. The resulting residue was purified by silica gel column chromatography (hexane: ethyl acetate=2:1-1:1-1:2 (volume ratio)) to obtain the title compound (293 mg, yield: 61.7%, copper content: 7 ppm).

$^1$H-NMR(CDCl$_3$): δ 0.85–1.05(9H,m), 1.2–1.8(22H,m), 2.05(2H,m), 2.25(2H,t,J=7.5Hz), 2.35–2.45(3H,m), 2.88 (1H,m), 3.05(1H,m), 4.05–4.15(4H,m), 5.4–5.65(2H,m).

EXAMPLE 2

Example of Preparation of Purified Methyl 9-acetoxy-11α, 15-bis(t-butyldimethylsiloxy)prosta-8,13E-dien-1-oate The same reaction was carried out to obtain methyl 9-acetoxy-11α,15S-bis (t-butyldimethylsiloxy)prosta-8,13E-dien-1-oate (copper content: 5 ppm), except that (4R)-t-butyldimethylsiloxy-2-(6-methoxycarbonylhexyl)-2-cyclopenten-1-one was used instead of (4R)-t-butyldimethylsiloxy-2-(6-butoxycarbonylhexyl)-2-cyclopenten-1-one of Example 1, and acetic anhydride was used instead of butyric anhydride.

$^1$H-NMR(CDCl$_3$): δ 0.0–0.1(15H,m), 0.7–0.8(18H,m), 1.1–2.4(21H,m), 2.0(3H,m), 2.65–2.95(2H,m), 3.55(3H,s), 3.95–4.00(2H,m), 5.20–5.50(2H,m).

EXAMPLE 3

Comparative Example

The same operation as in Example 1 was carried out except that the step of adding 2,2'-bipyridyl (2.06 g, 13.2 mmol), followed by stirring for 5 minutes, was omitted. The copper content was 26 ppm in the end compound.

According to the method of the present invention, a copper compound derived from an organic copper reagent to be used for a reaction of forming a skeleton, can be efficiently removed by a simple method. The copper content contained in the obtained PG derivative (formula 6) can be made extremely low, whereby the PG derivative (formula 6) may be used as a material for pharmaceuticals as it is.

What is claimed is:

1. A process for producing a purified prostaglandin derivative, which comprises adding an alkene represented by the following formula (1) to a cyclopentenone represented by the following formula (2) under the action of an alkyllithium and an organic copper reagent to form an adduct, reacting said adduct with a carboxylic acid halide represented by the following formula (3), a carboxylic anhydride represented by the following formula (4) or a mixed carboxylic anhydride represented by the following formula (5) to obtain a reaction product containing a prostaglandin derivative represented by the following formula 6, and then treating said reaction product with a nitrogen-containing compound:

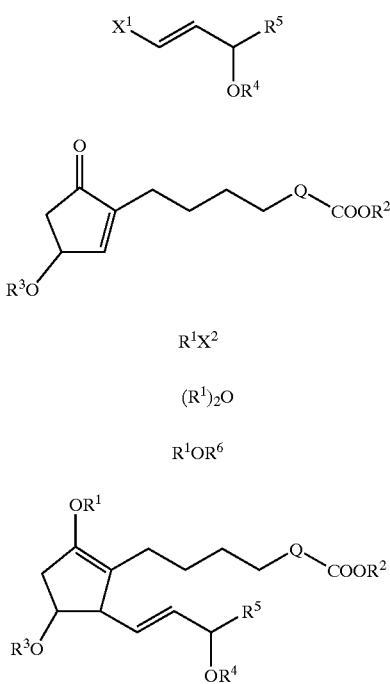

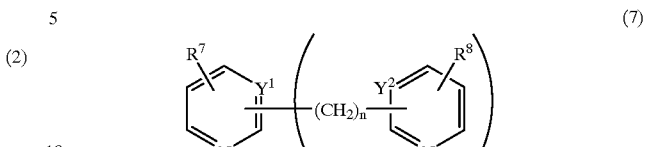

wherein
- $R^1$ is an alkanoyl group or an alkanoyl group containing a hereto atom in the alkyl group moiety,
- $R^2$ is an alkyl group or an alkyl group containing a hereto atom,
- each of $R^3$ and $R^4$ which are independent of each other, is a protecting group for a hydroxyl group or a hydrogen atom,
- $R^5$ is an alkyl group, a substituted alkyl group, a cycloalkyl group, a substituted cycloalkyl group, an alkenyl group or an alkynyl group,
- $R^6$ is an alkanoyl group or an alkanoyl group containing a hereto atom in an alkyl group moiety, and is different from $R^1$,
- Q is an ethylene group or a vinylene group,
- $X^1$ is an iodine atom or a trialkyltin group,
- $X^2$ is a halogen atom, and
- wherein the nitrogen-containing compound is selected from the group consisting of
  - (a) an organic carboxylic acid amide compound,
  - (b) an organic thiourea compound,
  - (c) an organic phosphorous triamide compound,
  - (d) an organic phosphoric triamide compounds, and
  - (e) an organic amine compound selected from the group consisting of trimethylamine, triethylamine, triisopropylamine, tributylamine, trioctylamine, cyclohexylamine, pyrrolidine, piperidine, N-methylcyclohexylamine, aniline, N-methylaniline, and N,N-dimethylaniline.

2. The process according to claim 1, wherein a deprotecting reaction is carried out after the treatment with the nitrogen-containing compound, to obtain the prostaglandin derivative of the formula (6) wherein at least one of $R^3$ and $R^4$ is a hydrogen atom, and wherein the amount of the nitrogen-containing compound is from 1 to 100 times the molar quantity of the organic copper reactant.

3. The process according to claim 1, wherein the aromatic heterocyclic compound having a nitrogen atom as a hetero atom, is a compound represented by the formula (7):

wherein
- each of $R^7$ and $R^8$ which are independent of each other is a hydrogen atom or an alkyl group,
- each of $Y^1$ and $Y^2$ which are independent of each other, is a nitrogen atom or CH, provided that $Y^1$ to which $R^7$ is bonded is C, and $Y^2$ to which $R^8$ is bonded is C,
- n is an integer of from 0 to 5, and
- m is an integer of from 1 to 3.

4. The process according to claim 1 or 2, wherein the means of treating the reaction product with a nitrogen-containing compound is a method of mixing the reaction product with the nitrogen-containing compound, followed by stirring.

5. The process according to claim 1 or 2, wherein the temperature during the treatment of the reaction product with a nitrogen-containing compound is from −20° C. to room temperature.

6. The process according to claim 1 or 2, wherein the purified prostaglandin derivative contains substantially from 0 ppm to 100 ppm of copper based on the prostaglandin derivative.

7. The process according to claim 1 or 2, wherein the prostaglandin derivative represented by the formula 6 is butyl 9-butanoyloxy-11α, 15S-dihydroxyprosta-8,13E-dien-1-oate.

8. The process according to claim 1, wherein the nitrogen-containing compound is the organic carboxylic acid amide compound.

9. The process according to claim 1, wherein the nitrogen-containing compound is the organic thiourea compound.

10. The process according to claim 1, wherein the nitrogen-containing compound is the organic phosphorous triamide compound.

11. The process according to claim 1, wherein the nitrogen-containing compound is the organic phosphoric triamide compound.

12. The process according to claim 1, wherein the nitrogen-containing compound is the organic amine compound.

13. The process according to claim 1, wherein the alkyl lithium is t-butyl lithium.

14. The process according to claim 1, wherein the organic copper reagent is a trialkylphosphine-copper iodide (I) complex.

15. The process according to claim 1, wherein the nitrogen-containing compound is thiourea, 1,3-dimethyl-2-thiourea, or 1,1,3,3-tetramethyl-2-thiourea.

16. The process according to claim 1, wherein the nitrogen-containing compound is hexamethylphosphorous triamide or hexaethylphosphorous triamide.

17. The process according to claim 1, wherein the nitrogen-containing compound is hexamethylphosphoric triamide or hexaethylphosphoric triamide.

18. The method of claim 1, wherein the amount of the nitrogen-containing compound is from 1 to 100 times the molar quantity of the organic copper reactant.

19. The method of claim 8, wherein the amount of the nitrogen-containing compound is from 1 to 100 times the molar quantity of the organic copper reactant.

20. The method of claim 9, wherein the amount of the nitrogen-containing compound is from 1 to 100 times the molar quantity of the organic copper reactant.

21. The method of claim 10, wherein the amount of the nitrogen-containing compound is from 1 to 100 times the molar quantity of the organic copper reactant.

22. The method of claim 11, wherein the amount of the nitrogen-containing compound is from 1 to 100 times the molar quantity of the organic copper reactant.

23. The method of claim 12, wherein the amount of the nitrogen-containing compound is from 1 to 100 times the molar quantity of the organic copper reactant.

* * * * *

UNITED STATES PATENT AND TRADEMARK OFFICE
CERTIFICATE OF CORRECTION

PATENT NO.     : 6,632,958 B1
DATED          : October 14, 2003
INVENTOR(S)    : Urushihara et al.

It is certified that error appears in the above-identified patent and that said Letters Patent is hereby corrected as shown below:

<u>Title page,</u>
Item [73], should read:
-- [73] Assignees:    Asahi Glass Company, Ltd. Tokyo (JP);
                     LTT Institute Co., Ltd. Tokyo (JP);
                     Mitsubishi Pharma Corporation, Osaka (JP) --.

Signed and Sealed this

Twenty-ninth Day of November, 2005

JON W. DUDAS
*Director of the United States Patent and Trademark Office*